United States Patent
Hu et al.

(10) Patent No.: US 8,841,490 B2
(45) Date of Patent: Sep. 23, 2014

(54) METHOD FOR PREPARING 3,3-DIMETHYLBUTYRALDEHYDE

(71) Applicant: Jinan Chenghuishuangda Chemical Industry Co., Ltd., Jinan (CN)

(72) Inventors: Junfeng Hu, Jinan (CN); Donghai Yu, Jinan (CN); Qingqian Jiang, Jinan (CN); Yanjun Yang, Jinan (CN)

(73) Assignee: Jinan Chenghuishuangda Chemical Industry Co., Ltd., Jinan (CN)

( * ) Notice: Subject to any disclaimer, the term of this patent is extended or adjusted under 35 U.S.C. 154(b) by 0 days.

(21) Appl. No.: 14/144,452

(22) Filed: Dec. 30, 2013

(65) Prior Publication Data

US 2014/0114091 A1    Apr. 24, 2014

Related U.S. Application Data

(63) Continuation-in-part of application No. PCT/CN2012/075098, filed on May 4, 2012.

(30) Foreign Application Priority Data

Aug. 16, 2011    (CN) .......................... 2011 1 0233967

(51) Int. Cl.
   *C07C 45/51*    (2006.01)
   *C07C 45/54*    (2006.01)
   *C07C 45/41*    (2006.01)
   *C07C 45/52*    (2006.01)

(52) U.S. Cl.
   CPC ................. *C07C 45/41* (2013.01); *C07C 45/52* (2013.01)
   USPC .......................................... 568/484; 568/488

(58) Field of Classification Search
   CPC ................................ C07C 45/54; C07C 45/41
   USPC .................................................. 568/484, 488
   See application file for complete search history.

(56) References Cited

U.S. PATENT DOCUMENTS 5,905,175 A * 5/1999 Guo et al. ..................... 568/490

OTHER PUBLICATIONS

Wu et al. Novel Synthetic Methods for Neotame and 3,3-Dimethyl Butyraldehyde, Chemical Industry Times, 2009, vol. 23, No. 7, pp. 16-19.*

* cited by examiner

*Primary Examiner* — Sikarl Witherspoon
(74) *Attorney, Agent, or Firm* — Matthias Scholl P.C.; Matthias Scholl

(57) ABSTRACT

A method for preparing 3,3-dimethylbutyraldehyde. The method includes: providing t-butyl chloride and vinyl acetate as raw materials, conducting a catalytic reaction between the t-butyl chloride and vinyl acetate to yield 1-chloro-3,3-dimethyl butyl acetate in the presence of a catalyst, the weight ratio of t-butyl chloride to vinyl acetate being 1:0.84-0.93; and controlling a temperature at between 100 and 110° C. for conducting hydrolytic disproportionation of 1-chloro-3,3-dimethyl butyl acetate in the presence of the catalyst to yield a mixture comprising 3,3-dimethylbutyraldehyde; and purifying the mixture by distillation to yield 3,3-dimethylbutyraldehyde, in which, the catalyst is aluminum trichloride, p-toluene sulphonic acid, or iron trichloride.

3 Claims, 1 Drawing Sheet

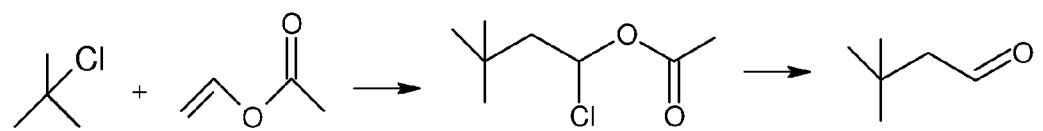

METHOD FOR PREPARING 3,3-DIMETHYLBUTYRALDEHYDE

CROSS-REFERENCE TO RELATED APPLICATIONS

This application is a continuation-in-part of International Patent Application No. PCT/CN2012/075098 with an international filing date of May 4, 2012, designating the United States, now pending, and further claims priority benefits to Chinese Patent Application No. 201110233967.0 filed Aug. 16, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to a method for preparing 3,3-dimethylbutyraldehyde as an intermediate for producing a sweetener.

2. Description of the Related Art

Neotame is a sweetener characterized by high sweetness and low cariogenicity. It has a great market potential and has been produced by different methods. However, as an important intermediate for producing the Neotame, 3,3-dimethylbutyraldehyde is relatively expensive.

A typical method for preparing 3,3-dimethylbutyraldehyde employs ethylene gas as the raw material. However, ethylene gas imposes high requirements on the transportation, storage, and production device, and risk exists in the transportation and the production process. The conventional preparation method is long and energy consuming, employs an inactive gas as a carrier to gasify a mixture of 3,3-dimethylbutyraldehyde and water at a temperature of above 300° C., and utilizes dehydrogenation in the presence of a precious metal. The method has low safety and high production cost. 3,3-dimethylbutyl chloride is expensive, and the resulting dimethyl thioethers cause environmental pollution.

SUMMARY OF THE INVENTION

In view of the above problems, it is one objective of the invention to provide a method for preparing 3,3-dimethylbutyraldehyde. The method has a low cost, employs accessible raw material, and employs a two-step controllable reaction to obtain 3,3-dimethylbutyraldehyde.

In accordance with an exemplary embodiment of the invention, provided is a method for preparing 3,3-dimethylbutyraldehyde. The method comprises: providing a t-butyl chloride and vinyl acetate as raw materials, conducting a catalytic reaction between the t-butyl chloride and vinyl acetate to yield 1-chloro-3,3-dimethyl butyl acetate in the presence of a catalyst, in which, a weight ratio of t-butyl chloride to vinyl acetate is 1:0.84-0.93; and controlling a temperature at between 100 and 110° C. for conducting hydrolytic disproportionation of 1-chloro-3,3-dimethyl butyl acetate in the presence of the catalyst to yield a mixture comprising 3,3-dimethylbutyraldehyde; and purifying the mixture by distillation to yield 3,3-dimethylbutyraldehyde, in which, the catalyst is aluminum trichloride, p-toluene sulphonic acid, or iron trichloride.

In a class of this embodiment, the method for preparing 3,3-dimethylbutyraldehyde is conducted as follows:

1) 50 kg of dichloromethane is added to a first reactor, stirred and cooled to a temperature of between −7° C. and 2° C. 1.3 kg of aluminum trichloride is added, 20 kg of t-butyl chloride is dropped within 3 hr, and 18.6 kg of vinyl acetate is dropped within 2 hr to yield a mixture. The mixture is allowed to react at a temperature of between −2° C. and 0° C. for 2 hr. After the reaction, 14 kg of deionized water is added to the first reactor and stirred completely. An organic phase is separated and washed using 6.7 kg of a 5% sodium carbonate solution until a PH value reaches between 8 and 9. The dichloromethane organic phase is collected and added with 5 kg of anhydrous sodium sulfate for desiccation. Dichloromethane is condensed and recovered at a temperature of between 30° C. and 50° C. and the organic phase is distilled under vacuum, a first fraction is collected at 60-64° C./20 mmHg. 35.7 kg of 1-chloro-3,3-dimethylbutyl acetate is obtained, and yield thereof is 92.5 wt. %.

2) The 35.7 kg of 1-chloro-3,3-dimethylbutyl acetate is added to a second reactor, 10 kg of a 10% hydrochoric acid is added, and a resulting mixture is heated to a temperature of between 100° C. and 110° C. and refluxed for 3 hr. Thereafter, the mixture is further heated, a second fraction at a temperature of between 104° C. and 106° C. is collected. 19.4 kg of 3,3-dimethylbutyraldehyde is obtained; a purity of the product is 99.6 wt. %, and a yield thereof is 96.7 wt. %.

In a class of this embodiment, the method for preparing 3,3-dimethylbutyraldehyde is conducted as follows:

1) 225 kg of dichloromethane is added to a first reactor, stirred and cooled to a temperature of between −7° C. and 2° C. 9 kg of p-toluene sulphonic acid is added, 80 kg of t-butyl chloride is dropped within 2 hr, and 70 kg of vinyl acetate is dropped within 2 hr to yield a mixture. The mixture is allowed to react at a temperature of between −2° C. and 0° C. for 2 hr. After the reaction, 56 kg of deionized water is added to the first reactor and stirred completely. An organic phase is separated and washed using 25 kg of a 5% sodium carbonate solution until a PH value reaches between 8 and 9. The dichloromethane organic phase is collected and added with 15 kg of anhydrous sodium sulfate for desiccation. Dichloromethane is condensed and recovered at a temperature of between 30° C. and 50° C. and the organic phase is distilled under vacuum, a first fraction is collected at 60-64° C./20 mmHg. 131.7 kg of 1-chloro-3,3-dimethylbutyl acetate is obtained, and a yield thereof is 90.7 wt. %.

2) The 131.7 kg of 1-chloro-3,3-dimethylbutyl acetate is added to a second reactor, 17 kg of a 15% phosphoric acid is added, and a resulting mixture is heated to a temperature of between 100° C. and 110° C. and refluxed for 3 hr. Thereafter, the mixture is further heated, a second fraction at a temperature of between 104° C. and 106° C. is collected. 70.1 kg of 3,3-dimethylbutyraldehyde is obtained, a purity of the product is 99.7 wt. %, and a yield thereof is 95 wt. %.

Advantages of the invention are as follows:

The raw materials and the reactions of the method of the invention is differentiated from the prior art in that the method of the invention selects low-priced t-butyl chloride and vinyl acetate as the raw materials, so that the price of the product is largely lowered, and the raw materials have relatively high safety in the transportation and storage. Besides, the method of the invention has a short procedure, moderate reaction conditions, no requirement on high temperature and on production device, high safety on the production. The purity of the product exceeds 99.7%, and a yield reaches 95%. Finally, the whole preparation method avoids environmental pollution resulting from by by-products, such as thioethers. The invention also features easy operation and easy control of different process parameters.

BRIEF DESCRIPTION OF THE DRAWINGS

The invention is described hereinbelow with reference to accompanying drawings, in which the sole FIGURE is a chemical reaction equation of the invention.

DETAILED DESCRIPTION OF THE EMBODIMENTS

A method for preparing 3,3-dimethylbutyraldehyde, comprises: providing t-butyl chloride and vinyl acetate as raw materials, conducting a catalytic reaction between a t-butyl chloride and vinyl acetate to yield 1-chloro-3,3-dimethyl butyl acetate in the presence of a catalyst, in which, a weight ratio of the t-butyl chloride to vinyl acetate is 1:0.84-0.93; and controlling a temperature at between 100 and 110° C. for conducting hydrolytic disproportionation of 1-chloro-3,3-dimethyl butyl acetate in the presence of the catalyst to yield a mixture comprising 3,3-dimethylbutyraldehyde; and purifying the mixture by distillation to yield 3,3-dimethylbutyraldehyde, in which, the catalyst is aluminum trichloride, p-toluene sulphonic acid, or iron trichloride.

Example 1

A method for preparing 3,3-dimethylbutyraldehyde is conducted as follows:

1) 50 kg of dichloromethane is added to a 100 L enamel reactor, stirred and cooled to a temperature of between −7° C. and 2° C. 1.3 kg of aluminum trichloride is added, 20 kg of t-butyl chloride is dropped within 3 hr, and 18.6 kg of vinyl acetate is dropped within 2 hr to yield a mixture. The mixture is allowed to react at a temperature of between −2° C. and 0° C. for 2 hr.

After the reaction, 14 kg of deionized water is added to the reactor and stirred completely. An organic phase is separated and washed using 6.7 kg of a 5% sodium carbonate solution until a PH value reaches between 8 and 9. The dichloromethane organic phase is collected and added with 5 kg of anhydrous sodium sulfate for desiccation. Dichloromethane is condensed and recovered at a temperature of between 30° C. and 50° C. and the organic phase is distilled under vacuum, a first fraction is collected at 60-64° C./20 mmHg. 35.7 kg of 1-chloro-3,3-dimethylbutyl acetate is obtained, and yield thereof is 92.5 wt. %.

2) The 35.7 kg of 1-chloro-3,3-dimethylbutyl acetate is added to a 50 L enamel reactor, 10 kg of a 10% hydrocholoric acid is added, a resulting mixture is heated to a temperature of between 100° C. and 110° C. and refluxed for 3 hr. Thereafter, the mixture is further heated, a second fraction at a temperature of between 104° C. and 106° C. is collected. 19.4 kg of 3,3-dimethylbutyraldehyde is obtained; a purity of the product is 99.6 wt. %, and a yield thereof is 96.7 wt. %.

Example 2

A method for preparing 3,3-dimethylbutyraldehyde is conducted as follows:

1) 225 kg of dichloromethane is added to a 500 L enamel reactor, stirred and cooled to a temperature of between −7° C. and 2° C. 9 kg of p-toluene sulphonic acid is added, 80 kg of t-butyl chloride is dropped within 2 hr, and 70 kg of vinyl acetate is dropped within 2 hr to yield a mixture. The mixture is allowed to react at a temperature of between −2° C. and 0° C. for 2 hr.

After the reaction, 56 kg of deionized water is added to the reactor and stirred completely. An organic phase is separated and washed using 25 kg of a 5% sodium carbonate solution until a PH value reaches between 8 and 9. The dichloromethane organic phase is collected and added with 15 kg of anhydrous sodium sulfate for desiccation. Dichloromethane is condensed and recovered at a temperature of between 30° C. and 50° C. and the organic phase is distilled under vacuum, a first fraction is collected at 60-64° C./20 mmHg. 131.7 kg of 1-chloro-3,3-dimethylbutyl acetate is obtained, and a yield thereof is 90.7 wt. %.

2) The 131.7 kg of 1-chloro-3,3-dimethylbutyl acetate is added to a 300 L enamel reactor, 17 kg of a 15% phosphoric acid is added, a resulting mixture is heated to a temperature of between 100° C. and 110° C. and refluxed for 3 hr. Thereafter, the mixture is further heated, a second fraction at a temperature of between 104° C. and 106° C. is collected. 70.1 kg of 3,3-dimethylbutyraldehyde is obtained, a purity of the product is 99.7 wt. %, and a yield thereof is 95 wt. %.

Example 3

A method for preparing 3,3-dimethylbutyraldehyde is conducted as follows:

1) 1200 kg of dichloromethane is added to a 3000 L enamel reactor, stirred and cooled to a temperature of between −7° C. and 2° C. 55 kg of iron trichloride is added, 480 kg of t-butyl chloride is dropped within 2 hr, and 405.7 kg of vinyl acetate is dropped within 2 hr to yield a mixture. The mixture is allowed to react at a temperature of between −2° C. and 0° C. for 2 hr.

After the reaction, 320 kg of deionized water is added to the reactor and stirred completely. An organic phase is separated and washed using 160 kg of a 5% sodium carbonate solution until a PH value reaches between 8 and 9. The dichloromethane organic phase is collected and added with 100 kg of anhydrous sodium sulfate for desiccation. Dichloromethane is condensed and recovered at a temperature of between 30° C. and 50° C. and the organic phase is distilled under vacuum, a first fraction is collected at 60-64° C./20 mmHg. 773 kg of 1-chloro-3,3-dimethylbutyl acetate is obtained, and a yield thereof is 91.8 wt. %.

2) The 773 kg of 1-chloro-3,3-dimethylbutyl acetate is added to a 1500 L enamel reactor, 100 kg of a 15% sulphuric acid is added, a resulting mixture is heated to a temperature of between 100° C. and 110° C. and refluxed for 3 hr. Thereafter, the mixture is further heated, a second fraction at a temperature of between 104° C. and 106° C. is collected. 405 kg of 3,3-dimethylbutyraldehyde is obtained, and a purity of the product is 99.8 wt. %, and a yield thereof is 95.5 wt. %.

Unless otherwise indicated, the numerical ranges involved in the invention include the end values.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing 3,3-dimethylbutyraldehyde, the method comprising:

1) providing a t-butyl chloride and vinyl acetate as raw materials, conducting catalytic reaction between the t-butyl chloride and vinyl acetate to yield 1-chloro-3,3-dimethyl butyl acetate in the presence of a catalyst, wherein, a weight ratio of the t-butyl chloride to vinyl acetate is 1:0.84-0.93; and 2) controlling a temperature at between 100 and 110° C. for conducting hydrolytic disproportionation of 1-chloro-3,3-dimethyl butyl acetate in the presence of the catalyst to yield a mixture comprising 3,3-dimethylbutyraldehyde; and purifying the mixture by distillation to yield 3,3-dimethylbutyraldehyde, wherein, the catalyst is aluminum trichloride, p-toluene sulphonic acid, or iron trichloride.

2. The method according to claim 1, wherein:

1) 50 kg of dichloromethane is added to a first reactor, stirred and cooled to a temperature of between −7° C. and 2° C.; 1.3 kg of aluminum trichloride is added, 20 kg of t-butyl chloride is dropped within 3 hr, and 18.6 kg of vinyl acetate is dropped within 2 hr to yield a mixture; and the mixture is allowed to react at a temperature of between −2° C. and 0° C. for 2 hr;

after the reaction, 14 kg of deionized water is added to the first reactor and stirred completely; an organic phase is separated and washed using 6.7 kg of a 5% sodium carbonate solution until a PH value reaches between 8 and 9; a dichloromethane organic phase is collected and added with 5 kg of anhydrous sodium sulfate for desiccation;

dichloromethane is condensed and recovered at a temperature of between 30° C. and 50° C. and the organic phase is distilled under vacuum, a first fraction is collected at 60-64° C./20 mmHg, and 35.7 kg of 1-chloro-3,3-dimethylbutyl acetate is obtained; and 2) the 35.7 kg of 1-chloro-3,3-dimethylbutyl acetate is added to a second reactor, 10 kg of a 10% hydrocholoric acid is added, a resulting mixture is heated to a temperature of between 100° C. and 110° C. and refluxed for 3 hr; thereafter, the mixture is further heated, a second fraction at a temperature of between 104° C. and 106° C. is collected, and 19.4 kg of 3,3-dimethylbutyraldehyde is obtained.

3. The method according to claim 1, wherein:

1) 225 kg of dichloromethane is added to a first reactor, stirred and cooled to a temperature of between −7° C. and 2° C.; 9 kg of p-toluene sulphonic acid is added, 80 kg of t-butyl chloride is dropped within 2 hr, and 70 kg of vinyl acetate is dropped within 2 hr to yield a mixture; and the mixture is allowed to react at a temperature of between −2° C. and 0° C. for 2 hr;

after the reaction, 56 kg of deionized water is added to the first reactor and stirred completely; an organic phase is separated and washed using 25 kg of a 5% sodium carbonate solution until a PH value reaches between 8 and 9; a dichloromethane organic phase is collected and added with 15 kg of anhydrous sodium sulfate for desiccation;

dichloromethane is condensed and recovered at a temperature of between 30° C. and 50° C. and the organic phase is distilled under vacuum, a first fraction is collected at 60-64° C./20 mmHg, and 131.7 kg of 1-chloro-3,3-dimethylbutyl acetate is obtained; and 2) the 131.7 kg of 1-chloro-3,3-dimethylbutyl acetate is added to a second reactor, 17 kg of a 15% phosphoric acid is added, a resulting mixture is heated to a temperature of between 100° C. and 110° C. and refluxed for 3 hr; thereafter, the mixture is further heated, a second fraction at a temperature of between 104° C. and 106° C. is collected and 70.1 kg of 3,3-dimethylbutyraldehyde is obtained.

* * * * *